US006251072B1

(12) United States Patent
Ladak et al.

(10) Patent No.: US 6,251,072 B1
(45) Date of Patent: Jun. 26, 2001

(54) SEMI-AUTOMATED SEGMENTATION METHOD FOR 3-DIMENSIONAL ULTRASOUND

(75) Inventors: Hanif M. Ladak, Brantford; Jeremy D. Gill, London; David A. Steinman, London; Aaron Fenster, London, all of (CA)

(73) Assignee: Life Imaging Systems, Inc. (CA)

( * ) Notice: Subject to any disclaimer, the term of this patent is extended or adjusted under 35 U.S.C. 154(b) by 0 days.

(21) Appl. No.: 09/253,385

(22) Filed: Feb. 19, 1999

(51) Int. Cl.$^7$ ........................................................ A61B 8/00

(52) U.S. Cl. ............................................ 600/443; 128/916

(58) Field of Search .................................... 600/443, 447, 600/450; 128/916; 367/7, 11; 73/625

(56) References Cited

U.S. PATENT DOCUMENTS 5,601,084 * 2/1997 Sheehan et al. ..................... 600/450

OTHER PUBLICATIONS

Sherebrin, Shi, et al., Freehand Three–Dimensional Ultrasound: Implementation and Applications, *SPIE*, vol. 2708, pp. 296–303 (Feb. 1996).
Terzopoulos, Demetri, et al., Sampling and Reconstruction with Adaptive Meshes, *Proceedings of the Conference on Computer Vision and Pattern Recognition*, pp. 70–75 (Jun. 1991).
Fenster, Aaron, et al., 3–D Ultrasound Imaging: A Review, *IEEE Engineering in Medicine and Biology*, pp. 41–51 (Nov./Dec. 1996).
Barnett, et al., Beneficial Effect Of Carotid Endarterectomy In Symptomatic Patients With High–Grade Carotid Stenosis, *The New England Journal of Medicine*, vol 325, No. 7, pp. 445–453 (Aug. 1991).

I. Dehaene, et al., MRC European Carotid Surgery Trial: Interim Results For Symptomatic Patients With Severe (70–99%) Or With Mild (0–29%) Carotid Stenosis, *The Lancet*, vol. 337, No. 8752, pp. 1235–1243 (May 1991).
Gorelick, Philip B., MD, MPH, FACP, Stroke Prevention. An Opportunity For Efficient Utilization Of Health Care Resources During The Coming Decade, *Stroke*, vol. 25, No. 1, pp. 220–224 (Jan. 1994).
McInerney, Tim, et al., Deformable Models In Medical Image Analysis: A Survey, *Medical Image Analysis*, vol. 1, No. 2, pp. 91–108 (1996).
Chen, Yang, et al., Description Of Complex Objects From Multiple Range Images Using An Inflating Balloon Model, *Computer Vision and Image Understanding*, vol. 61, No. 3, pp. 325–334 (May 1995).
Young, Ian T., et al., Recursive Implementation Of The Gaussian Filter, *Signal Processing*, vol. 44, pp. 140–151 (1995).
Bouma, Carolien J., et al., Evaluation Of Segmentation Algorithms For Intravascular Ultrasound Images, *Lecture Notes in Computer Science*, vol. 1131, pp. 203–212 (1996).

(List continued on next page.)

*Primary Examiner*—Marvin M. Lateef
*Assistant Examiner*—Ali M. Imam
(74) *Attorney, Agent, or Firm*—Fulwider Patton Lee & Utecht, LLP

(57) ABSTRACT

The present invention provides a semi-automated method for three-dimensional ultrasound for constructing and displaying 3-D ultrasound images of luminal surfaces of blood vessels. The method comprises acquiring a 3-D ultrasound image of a target vessel and segmenting the luminal surfaces acquired from the 3-D ultrasound image of the target vessel to generate a 3-D ultrasound image of the lumen of the target vessel, wherein an inflating balloon model is used for segmenting the luminal surfaces of the target vessel. The method is useful for diagnostic assessment of bodily vessels as well as provides for therapy planning and as a prognostic indicator.

14 Claims, 7 Drawing Sheets

OTHER PUBLICATIONS

Carrascal, Francisco M., et al., Automatic Calculation Of Total Lung Capacity From Automatically Traced Lung Boundaries In Postero–Anterior And Lateral Digital Chest Radiographs, *Medical Physics*, vol. 25, No. 7, pp. 1118–1131 (Jul. 1998).

Duryea, Jeff, et al., A Fully Automated Algorithm For The Segmentation Of Lung Fields On Digital Chest Radiographic Images, *Medical Physics*, vol. 22, No. 2, pp. 183–191 (Feb. 1995).

Miller, James V., et al., Geometrically Deformed Models: A Method For Extracting Closed Geometric Models From Volume Data, *Computer Graphics*, vol. 25, No. 4, pp. 217–226 (Jul. 1991).

Arbeille, Ph., MD, PhD, et al., Quantification and Assessment Of Carotid Artery Lesions: Degree Of Stenosis And Plaque Volume, *Journal of Clinical Ultrasound*, vol. 23, No. 2, pp. 113–124 (Feb. 1995).

Hatsukami, Thomas S., et al., Echolucent Regions In Carotid Plaque: Preliminary Analysis Comparing Three–Dimensional Histologic Reconstructions To Sonographic Findings, *Ultrasound in Medicine and Biology*, vol. 20, No. 8, pp. 743–749 (1994).

Lobregt, Steven, et al., A Discrete Dynamic Contour Model, *IEEE*, pp. 12–24 (1995).

Kass, Michael, et al., Snakes: Active Contour Models, *International Journal of computer Vision*, pp. 321–331 (1988).

Steinke, et al., Three–dimensional Ultrasound Imaging of Carotid Artery Plaque, *Journal of Cardiovascular Technology*, vol. 8, No. 1, pp. 15–22 (1989).

Gonzales et al., Digital Image Processing, *Addison–Wesley Publishing Company*, Second Edition, pp. 369–373 (1987).

* cited by examiner

SEMI-AUTOMATED SEGMENTATION METHOD FOR 3-DIMENSIONAL ULTRASOUND

FIELD OF THE INVENTION

The present invention relates to a semi-automated method for constructing and displaying 3-D ultrasound images. In particular, the semi-automated method provides 3-D ultrasound images of luminal surfaces of blood vessels.

BACKGROUND OF THE INVENTION

The severity of atherosclerosis at the carotid artery bifurcation is correlated with the occurrence of stroke.[1,2] Since most strokes associated with carotid atherosclerosis can be prevented by surgical or non-surgical treatment[3], the identification and monitoring of carotid disease is important for the management of patients at risk of stroke. Currently, conventional means of diagnosing and assessing the progression of atherosclerosis involve either determining the degree of stenosis with x-ray angiography or MRA, or with techniques which are sensitive to abnormalities in blood flow rate, such as Doppler ultrasonography. Unfortunately, none of these known techniques provide a clear three-dimensional (3-D) image of the target tissue in a manner which allows for the non-invasive and detailed view of the blood vessels. Moreover, none of the known techniques provide detailed visualization of the lumen surfaces of blood vessels within the body.

It is therefore an object of the present invention to provide a novel method, based on 3-D ultrasound, which is non-invasive and provides detailed three-dimensional views of internal luminal surfaces of blood vessels. An important task in the development of such a technique is the segmentation (i.e., extraction) of vessel surfaces from ultrasound images for the purposes of visualization, therapy planning, and volumetric measurements. Deformable surface models have become particularly useful tools for this method.[4]

SUMMARY OF THE INVENTION

According to one aspect of the present invention there is provided a semi-automatic 3-D ultrasound segmentation method for displaying luminal surfaces of vessels, the method comprising the steps of:

(a) acquiring a 3-D ultrasound image of a target vessel; and (b) segmenting the luminal surfaces from the 3-D ultrasound image of the target vessel to generate a 3-D ultrasound image of the lumen of the target vessel; wherein an inflating balloon model is used for segmenting the luminal surfaces of the target vessel.

In another aspect of the present invention, there is provided a method for the diagnosis and prognosis of vessel disease, the method comprising the steps of:

(a) acquiring a 3-D ultrasound image of a target vessel;

(b) segmenting the luminal surfaces from the 3-D ultrasound image of the target vessel to generate a 3-D ultrasound image of the lumen of the target vessel using an inflating balloon model;

(c) inspecting the generated 3-D ultrasound image of the lumen of the target vessel to assess the presence of a shadow representing a disease lesion within the lumen.

BRIEF DESCRIPTION OF THE DRAWINGS

FIG. 1(a) shows the edge 1-3 exceeds the user-specified threshold length while FIG. 1(b) shows the edge 1-3 is divided into two with new triangles being formed;

Figure 1:
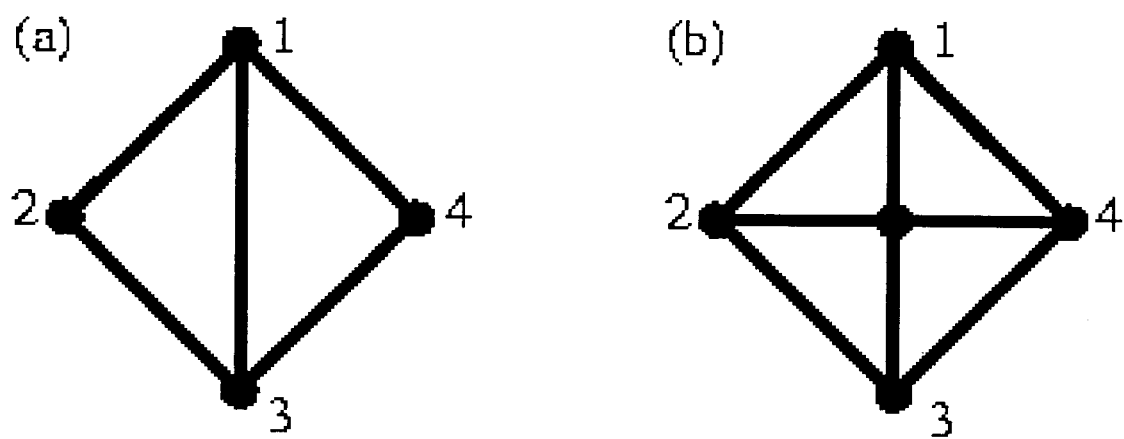
FIG. 1 illustrates the subdivision of a mesh used in the inflating balloon model.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENTS

According to an embodiment of the present invention, there is provided a 3-D semi-automatic segmentation method, based on a deformable model, for extracting and displaying the lumen surfaces of vessels from 3-D ultrasound images. The method uses a deformable model which first is rapidly inflated to approximate the boundary of the artery, the model is then further deformed using image-based forces to better localize the boundary. The method can be used in the diagnosis and prognosis of various diseases associated with blood vessels such as atherosclerosis.

The method requires that an operator select an arbitrary position within a target vessel, such as a carotid vessel, as a starting point for the development of the model. Since the choice of initialization position affects the subsequent development of the deformable model, there is variability in the final segmented boundary. The performance of the segmentation method has been tested by examining the local variability in boundary shape as the initial position is varied throughout the lumen of a 3-D ultrasound image of a carotid bifurcation. The test results indicate that high variability in boundary position occurs in regions where either the segmented boundary is highly curved or the 3-D ultrasound image has no well-defined vessel edges.

Acquisition of 3-D Ultrasound Images

A free-hand imaging system[5,6] was used to acquire 3-D ultrasound images of target vessels for use in the present method. The system makes use of a six-degree-of-freedom, DC magnetic, field-based POM device (Flock of Birds, Ascension Technologies) affixed to an ultrasound probe to track the position and orientation of the probe during the scan. Video frames from an ultrasound machine (Ultramark-9, Advanced Technology Laboratories) were digitized with a video-frame grabber (RasterOps 24XLTV, TrueVision) and saved to a Macintosh computer along with simultaneous recordings of the transducer orientation and position. Image reconstruction involves transforming each input image by a matrix which is determined from the recorded probe orientation during image acquisition. Applying the transformation matrix to each image converts the image to a global coordinate space. Once the images have been transformed, the spatial extent and resolution of the output 3-D image is determined. The final 3-D ultrasound image is reconstructed one slice at a time by determining the nearest input image pixel for each voxel. Gaps between image planes are filled in using nearest neighbor interpolation.[6] The final 3-D ultrasound image was then used as the basis for the segmentation of the target vessel surface.

Segmentation

An inflating balloon model[7] forms the basis of the present algorithm for segmenting the target vessels. Although the present method can be used to examine luminal surfaces of any fluid filled tissue, for the purposes of illustration, carotid arteries were used as the choice of vessel in the present method. The algorithm consists of three major steps: (1) interactive placement of the initial balloon model inside the lumen of the artery; (2) automatic inflation of the model towards the arterial wall; and, (3) automatic localization of the arterial wall. The balloon model is represented by a closed mesh of triangles, with the initial mesh being an icosahedron. After the initial model is placed inside the artery, it is rapidly inflated towards the arterial wall. When equilibrium under the influence of inflation forces is reached, the model approximately represents the shape of the artery. This approximate mesh is then further deformed by means of image-based forces to localize the wall of the artery. Equations describing the dynamics of the model and the forces acting on it are provided below.

(a) Dynamics

The equation of motion for vertex i of the mesh is given by[8]

$$m_i \ddot{x}_i(t) + v_i \dot{x}_i(t) + g(x_i(t)) = f(x_i(t)) \quad (1)$$

where $x_i(t)$ is the position of the vertex, $\dot{x}_i(t)$ and $\ddot{x}_i(t)$ are its velocity and acceleration, respectively, $m_i$ is its mass, $v_i$ is the damping coefficient, $g_i(x_i(t))$ is the resultant surface tension at the vertex and $f_i(x_i(t))$ is a "driving" force. Equilibrium is reached when both $\dot{x}_i(t)$ and $\ddot{x}_i(t)$ become zero, which can take a very long time. By setting the mass of each vertex to zero and the damping coefficient to unity, Equation (1) is reduced to:

$$\dot{x}_i(t) = f(x_i(t)) - g(x_i(t)) \quad (2)$$

The system represented by Equation (2) reaches equilibrium when xi(t) becomes zero, which can occur quickly since the system does not possess inertia. To compute the equilibrium position of each vertex, and hence the deformed shape of the model, Equation (2) is iteratively updated from time t to time t+Δt using the formula:

$$\dot{x}_i(t+\Delta t) \approx x_i(t) + (f(x_i(t)) - g(x_i(t)))\Delta t \quad (3)$$

Iterations continue until $\dot{x}_i(t)$ becomes approximately zero for all vertices. After each iteration, the triangles of the mesh grow in size. In order to model accurately the shape of the artery, the triangles of the mesh are subdivided to form smaller triangles. Essentially, after each iteration, the length of each edge in the mesh is compared to a user-specified threshold length. If the length exceeds the threshold, the edge is divided into two edges of equal length and the two triangles on either side of the original edge are replaced by four triangles as shown in FIG. 1.

(b) Driving Forces

In step (2) of the algorithm, the model is driven towards the arterial wall by means of an inflation force acting on each vertex i:

$$f_{Inf}(x_i(t)) = \begin{cases} k_{Inf} n_i(t), & \text{if } I(x_i(t)) \leq T \text{ and } x_i(t) \varepsilon VOI \\ 0, & \text{otherwise} \end{cases} \quad (4)$$

where $k_{Inf}$ is the amplitude of the inflation force and $n_i(t)$ is the normal at the vertex, which is computed as the average of the normals of each triangle attached to the vertex. The inflation force is turned on at vertices where the corresponding image intensity $I(x_i(t))$ is below a user-selected gray-level threshold T. In practice, the balloon model may leak outside the arterial wall since artifacts such as acoustic shadows result in large voids adjacent to the artery, which have the same mean gray level as the lumen. The occurrence of a calcified lesion on the lumen of the carotid vessels is one such cause of shadow. To prevent the model from growing too far beyond the arterial wall, the inflation force is only applied for points which are inside a user-defined volume of interest (VOI). The VOI is modeled as the union of simple geometric shapes, constructed from cylinders with rounded ends. The complete VOI is formed by joining five such shapes, individually sized and oriented to fit the carotid vessel.

Figure 2:
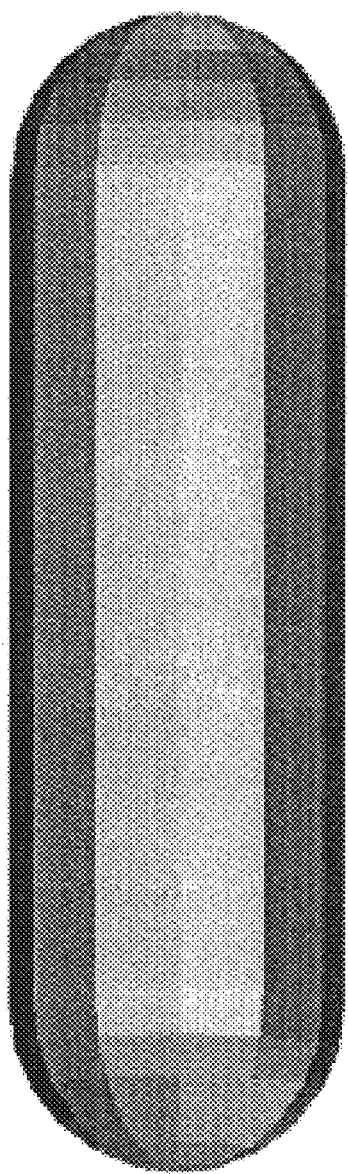
FIG. 2 illustrates two views of a primitive shape consisting of a cylinder and two hemispherical end-caps used to generate a 3-D volume of interest (VOI)
Figure 2:
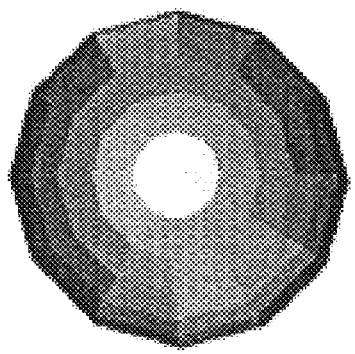
Figure 3:
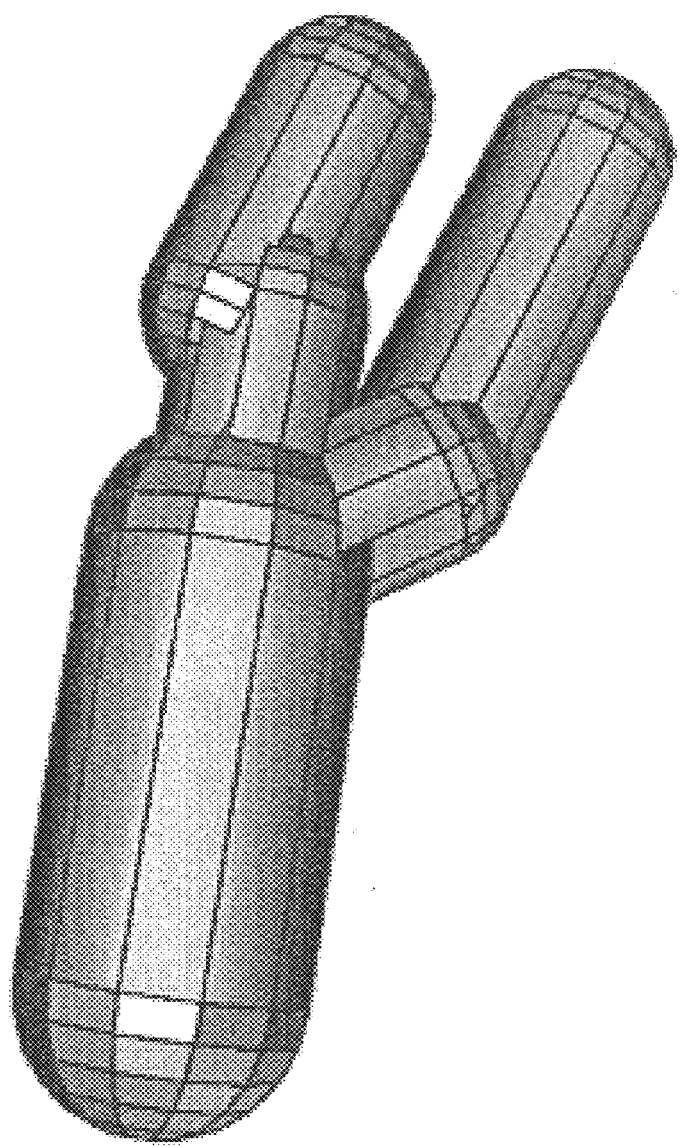
FIG. 3 illustrates a 3-D volume of interest (VOI) constructed from five primitive shapes, each basic shape is scaled and stretched to fit approximately into the carotid vessel.

A single geometric primitive is shown in FIG. 2 and the complete VOI used in this study is shown in FIG. 3. The boundary obtained by the application of an inflation force alone is an approximation to the actual wall of the artery since it is difficult to identify a threshold, which exactly separates points inside the lumen from those outside and because of the presence of artifacts. In step (3) of the algorithm, this approximation is refined. To localize the arterial wall better, a 3-D potential function (P) is constructed from the image data which attracts the model to 3-D intensity edges (gradients):

$$P(x_i(t)) = \frac{1}{\|(\nabla_\sigma * I)\| + \varepsilon} \quad (5)$$

where $G_\sigma$ is a 3-D Gaussian smoothing filter[9] of characteristic width σ sand ε is a small constant to prevent division by zero. Minima of the potential function coincide with the arterial wall. The potential function produces a force field which is used to deform the model:

$$f_{edge}(x_i(t)) = -k_{edge} \nabla P(x_i(t)) \quad (6)$$

where $k_{edge}$ controls the strength of the force.

(c) Surface Tension

Surface tension keeps the model smooth in the presence of noise. It is simulated by treating each edge of the model as a spring. Surface tension at vertex i is computed as the vector sum of each normalized edge vector connected to the vertex:

$$g(x_i(t)) = \frac{K_{tens}}{M} \sum_{j=1}^{M} \frac{e_{ij}}{\|e_{ij}\|}$$

where $e_{ij}=x_j(t)-x_i(t)$ is a vector representing the edge connecting vertex i to an adjacent vertex j, $k_{tens}$ controls the strength of the resultant tensile force, and M is the number of edges connected to vertex i.

Assessment of Variability

Accuracy is often used as the basis for assessing the performance of a segmentation method.[10-12] However, in cases where the segmented boundary depends on some form of operator initialization, boundary variability also plays an important role in judging performance. The present method requires that an operator selects an initialization position within the carotid vessel, which affects the final segmented boundary. Variability in the position and shape of the final segmented boundary occurs because the user-defined initialization position is arbitrary. For applications such as monitoring the progression of atherosclerosis over time or its regression due to non-surgical treatment, low variability assessment of the vessel boundary is required. Furthermore, assessment is particularly crucial at local regions with lesions. For this reason, a local measure of variability has been selected as a means of assessing the performance of our segmentation method. Only the variability associated with the choice of initialization position is considered and all other segmentation parameters remain constant throughout. The procedure involves: (1) generating an ensemble of meshes, which span the space of likely initialization positions; (2) determining an average segmentation boundary from the set of meshes; (3) determining a description of the spatial distribution of the meshes; and, (4) computing the variance of mesh locations on the surface of the average boundary. The steps involved in determining our measure of local variability are described in the following sections.

(i) Generating an Ensemble of Meshes

An ensemble of segmentation meshes is generated using different initialization positions for each mesh. The positions are spaced evenly throughout the interior of the carotid vessel. A point, x, is considered to lie within the vessel if it satisfies both conditions in equation (4), namely, $I(x) \leq T$ and $x \in VOI$. For the 3-D ultrasound image shown in FIG. 4 there are more than half a million voxel positions which satisfy these conditions. In order to reduce the required computing time for determining the ensemble of meshes, the set of suitable positions are subsampled by a factor of nine in each dimension, resulting in about 750 meshes. On a 600 Compaq Alpha workstation, mesh generation for all 750 positions takes about three hours.

(ii) Generating the Average Mesh

The procedure for determining the average of the ensemble of meshes is based on establishing a one-to-one correspondence between points in one mesh and points in every other mesh. The set of N meshes, $x_1, x_2, \ldots, x_N$, each have $M_N$ points. A mesh $X_1$ was randomly selected, and for each point $x_{i1}$ in $x_1$, the closest points $x_{i2}, x_{i3}, \ldots, x_{iN}$ in meshes $x_2, x_3, \ldots, x_N$ are found. A point, $y_i$ on the average mesh Y is found by determining the centroid of all corresponding points $x_{i2}, x_{i3}, \ldots, x_{iN}$.

$$y_i = \frac{1}{N} \sum_{j=1}^{N} x_{ji} \quad (8)$$

(iii) Generating the Boundary Density Function

In order to compute the statistical parameters associated with the variability of the 3-D segmentation, a discrete 3-D representation of the spatial distribution of the ensemble of meshes is first defined, which is called the boundary density function (BDF). The BDF has the same dimensions as the original ultrasound image and each voxel in the ultrasound image corresponds to a voxel in the BDF. Each voxel in the BDF is assigned a value which is equal to the number of segmented boundary meshes which intersect the equivalent voxel.

(iv) Variance Map as a Local Measure of Variability

Having both an average mesh, and a statistical description of the spatial distribution of meshes (i.e., the BDF), the variability in the segmentation algorithm can be determined. For each point $y_i$ on the average mesh, Y, the BDF is sampled at U discrete points along a line segment centered about $y_i$, and oriented in the direction of the surface normal, $n(y_i)$. This sampling procedure reduces the BDF into a set of one dimensional distributions, $D_i(u)$. Given a mesh point, $y_i$, and sampled BDF distribution for the point, $D_i(u)$, the variance $V_i$ of the sampled distribution at each point $y_i$ on the average mesh is:

$$V_i = \frac{1}{U} \sum_{u=0}^{U} (D_i - D_i(u))^2$$

and represents the measure of local variability in the segmentation procedure.

Acquisition of the 3-D Segmentated Ultrasound Image

Figure 4:
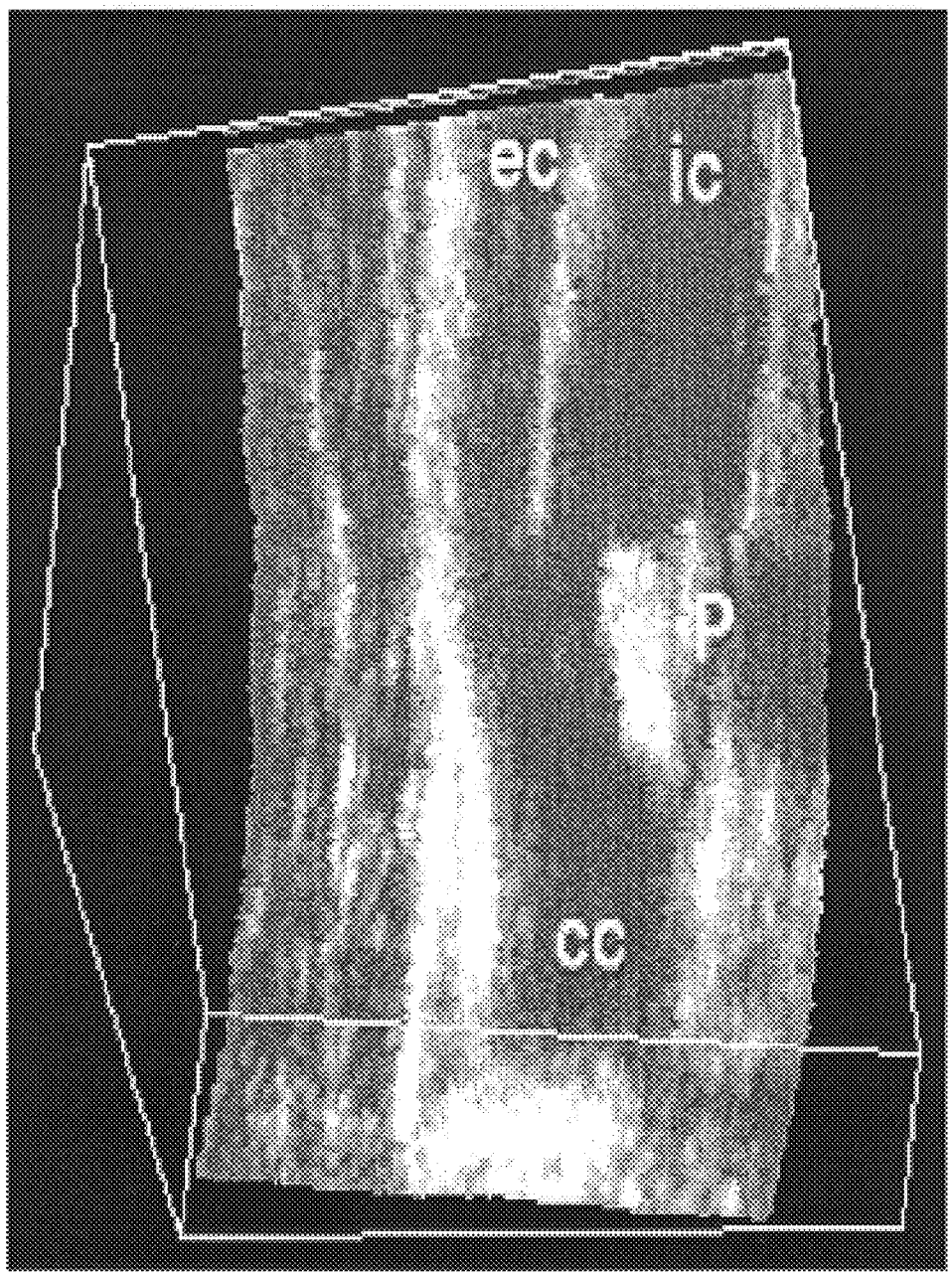
FIG. 4 illustrates a section through a 3-D ultrasound image of diseased carotid arteries showing a plaque (P) on the right-hand side of the image, the internal carotid (ic), external carotid (ec) and common carotid (cc) arteries are labeled.

FIG. 4 shows a slice through a freehand 3-D ultrasound image of a carotid bifurcation oriented approximately in the plane of the bifurcation. Ultrasound insonation occurred from the left-hand side of the image. A plaque is visible on the right-hand wall of the common carotid artery, and casts a shadow on the vessel wall, proximal to the bifurcation. Image values in the shadow portion of the ultrasound image are similar to those found within the carotid vessel, therefore, image value alone cannot be used to localize the boundary of the carotid lumen.

Figure 5:
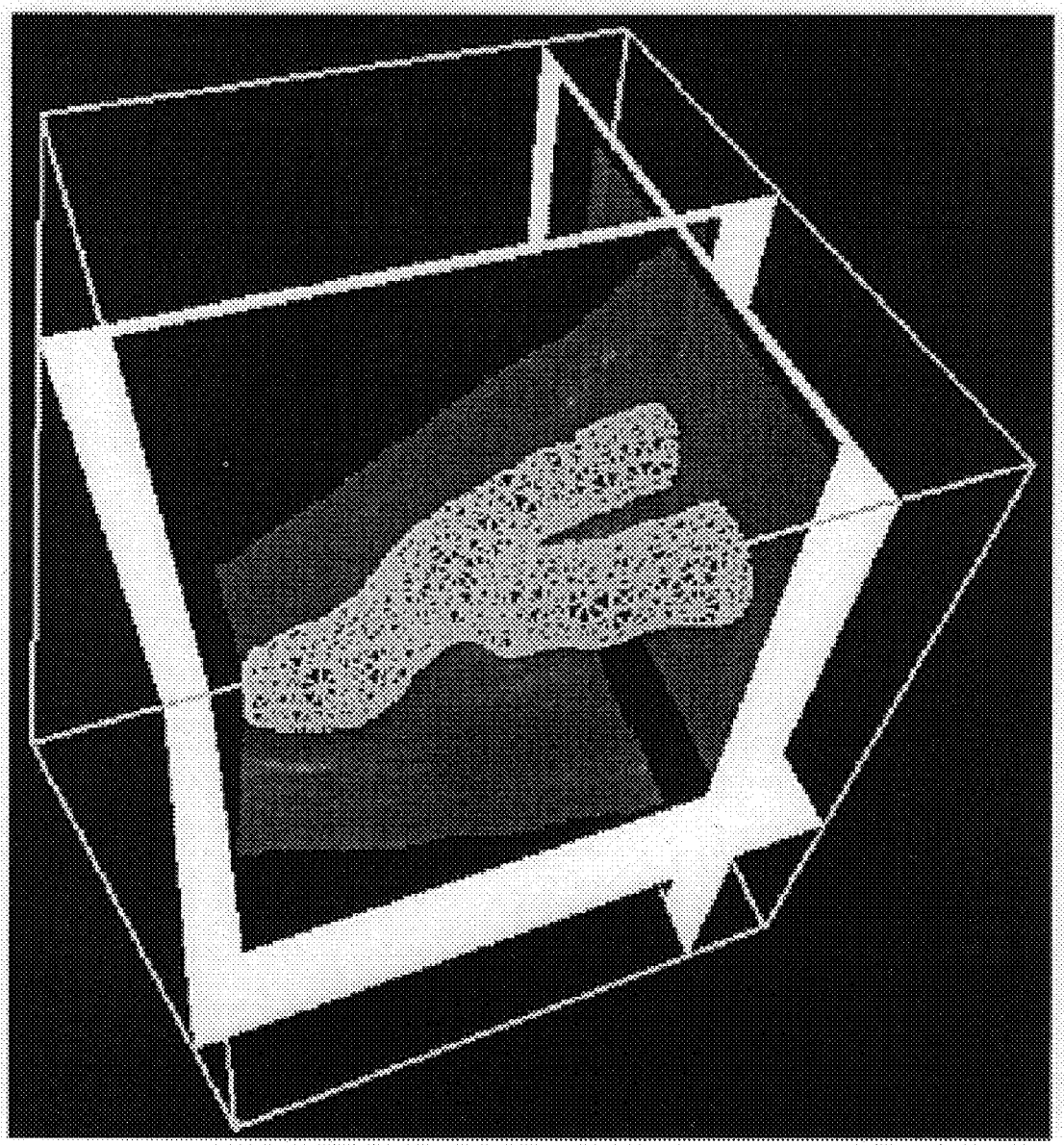
FIG. 5 illustrates a segmented boundary for the free-hand 3-D ultrasound image as made by the method disclosed herein and as shown in FIG. 4, the mesh is shown superimposed on three orthogonal slices through the ultrasound image.
Figure 6:
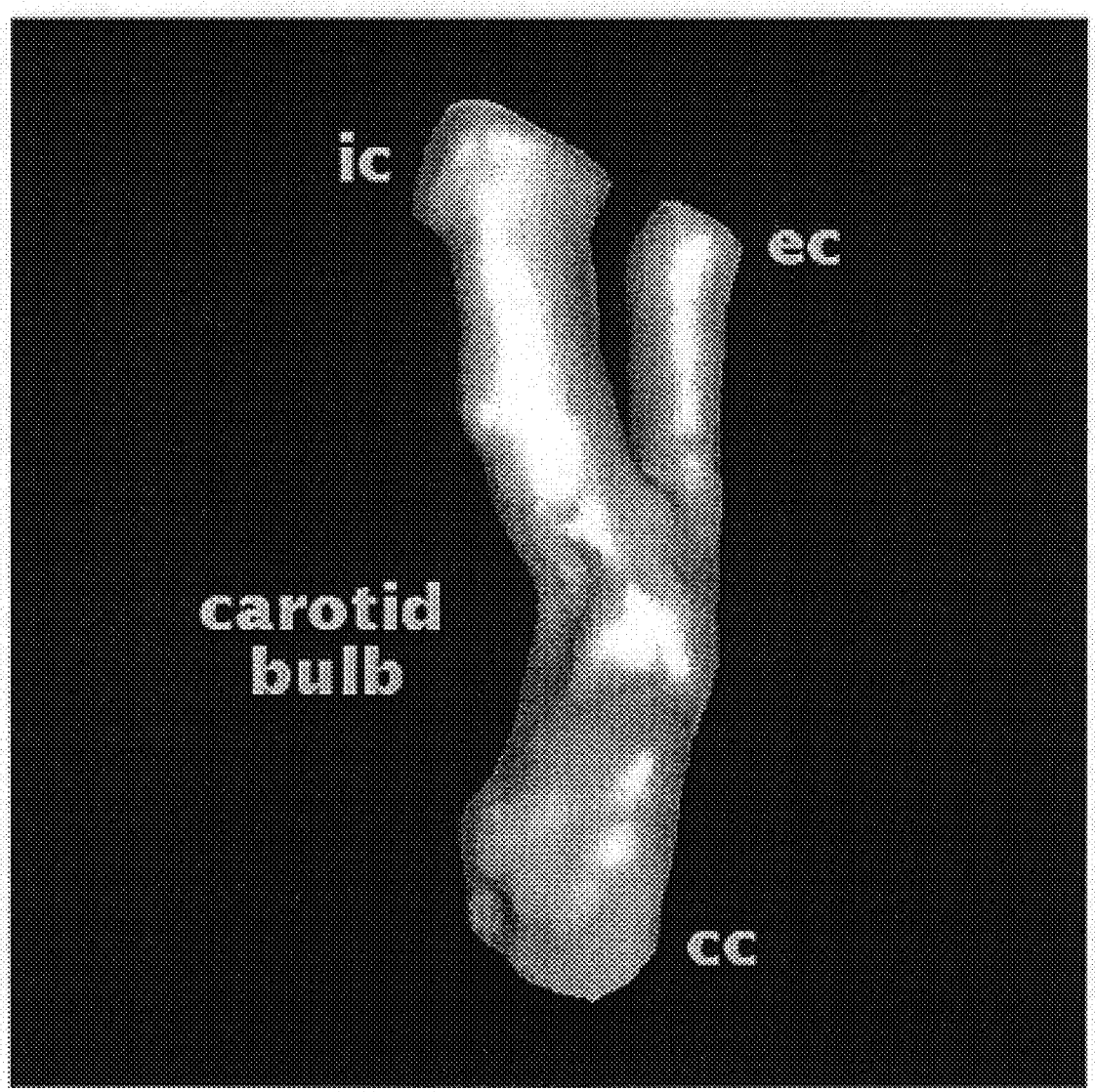
FIG. 6 illustrates the segmented boundary of the image of FIG. 4 shown as a rendered surface, the internal carotid (ic), external carotid (ec), common carotid (cc) and carotid bulb are indicated.

FIG. 5 shows a segmented boundary generated from the freehand 3-D ultrasound image shown in FIG. 4. Three orthogonal slices through the ultrasound image are also shown. FIG. 6 shows the same segmented boundary from a different orientation, illustrating that the plaque has reduced the diameter of vessel lumen near the carotid bulb.

Figure 7:
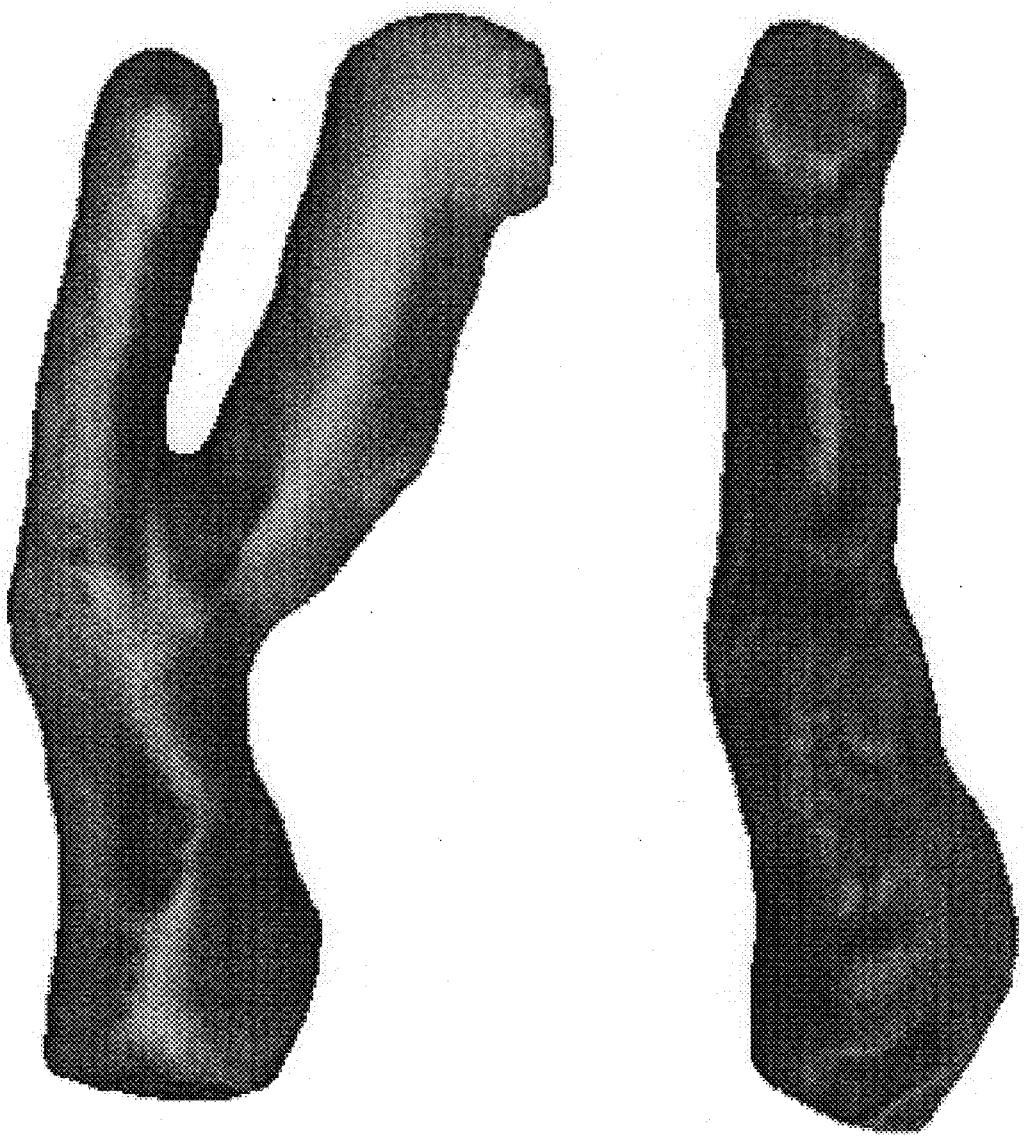
FIG. 7 illustrates a variance map for segmentation of a carotid vessel from a 3-D ultrasound image, showing high variability in mesh portion at the apex of the bifurcation, in two orientations of the same vessel.

FIG. 7 shows the local variability in the segmented boundary, determined by sampling the corresponding BDF about each point of the average boundary. In this figure, the average mesh is shown with shading which represents the local variance in mesh position, determined from the BDF. Dark regions correspond to high variability, while lighter regions have low variability. FIG. 7(a) shows that the apex of the bifurcation is a site of high variability, while FIG. 7(b) shows that there are other local regions of increased variability. The region corresponding to the calcified plaque appears to have low variability in mesh localization.

The method of the present invention is relatively simple and requires low computational overhead and thus segmentation occurs quite rapidly. A typical 256×256×256 voxel ultrasound image can be segmented in approximately 10 seconds on a modem workstation, once initial loading and filtering of the ultrasound image has been completed. However, the speed of segmentation requires significant computer resources in terms of memory storage. In order to gain speed, the entire volume is kept in main memory throughout the segmentation process. A Gaussian filtered copy of the image also is computed, followed by a three-component force vector field.

Image noise in the ultrasound image can prevent the deformable model from reaching the boundary of the target carotid artery during the stage when driving forces are applied to each mesh point. Spuriously high grey-level values (i.e., $I(x_i(t))>T$) will cause mesh points to stop moving prematurely.

The results show high variability in segmentation position is associated with regions of ultrasound image where the vessel boundary is not well defined (i.e., low contrast) and with regions of high curvature (such as at the apex of the bifurcation). The plaque boundary is well defined and thus the segmented boundaries have low variability in this region of the ultrasound image. Since user intervention in initializing the segmentation method results in variability in the segmented boundary shape, it is important to assess the performance of the segmentation method based on local variability. The present segmentation method based on a free-hand 3-D ultrasound image of the carotid vessels, shows a correlation between a mapping of the local variability in segmentation as a function of initial model position.

In summary, a semi-automatic method for extracting and displaying the lumen of vessels from 3-D ultrasound images has been developed. Such method allows for the rapid and simple non-invasive and clear visualization of the internal luminal surfaces of vessels. Specifically, the method allows for the diagnosis, prognosis and treatment of different types of disease lesions within body vessels.

It is understood by one skilled in the art, that the method of the present invention can be used to provide 3-D images of any luminal surface of any type of body channel that carries a biological fluid. That is, any fluid filled body tissue can be diagnostically analyzed using the method of the present invention, including for example tissue abscesses such as kidney or follicular. Body channels include for example but are not limited to vessels such as blood, lymph and lacteal as found in humans and/or animals. The method is particularly useful for the management and treatment of arterial disease (i.e., blood vessel) such as arterial atherosclerosis.

Variations and modifications of the present invention should be apparent to those of skill in the art without departing from the scope of the present invention as defined by the appended claims.

References

1. North American Symptomatic Carotid Endarterectomy Trial Collaborators, "Beneficial effect of carotid endarterectomy in symptomatic patients with high grade carotid stenosis," *New England J. Med* 325, pp.445–453, 1991.
2. European Carotid Surgery Trialists' Collaborative Group, "MRC European carotid surgery trial: Interim results for symptomatic patients with severe (70–99%) or with mild (0–29%) carotid stenosis," *Lancet* 337, pp. 1235–1243, 1991.
3. P. B. Gorelick, "Stroke prevention. an opportunity for efficient utilization of health care resources during the coming decade," *Stroke* 25, pp. 1581–1587, 1994.
4. T. McInerney and D. Terzopoulos, "Deformable models in medical image analysis: A survey," *Medical Image Analysis* 1(2), pp. 91–108, 1996.
5. A. Fenster and D. B. Downey, "3-d ultrasound imaging: A review," *IEEE Eng. Med. Biol.* 15, 1996.
6. S. Sherebrin, A. Fenster, R. Rankin, and D. Spence, "Freehand three-dimensional ultrasound: Implementation and applications," *SPIE Phys. Med Imag.* 2708, pp.296–303, 1996.
7. Y. Chen and G. Medioni, "Description of complex objects from multiple range images ultrasounding an inflating balloon model," *Comput. Vision and Image Understanding* 61, pp. 325–334, 1995.
8. D. Terzopoulos and M. Vasilescu, "Sampling and reconstruction with adaptive meshes," in *Proceedings of the Conference on Computer Vision and Pattern Recognition,* pp.70–75, June 1991.
9. I. T. Young and L. J. van Vliet, "Recursive implementation of the gaultrasoundsian filter," *Signal Processing* 44, pp. 139–151, 1995.
10. C. J. Bouma, W. J. Niessen, K. J. Zuiderveld, E. J. Gultrasoundsenhoven, and M. A. Viergever, "Evaluation of segmentation algorithms for intravascular ultrasound images," *Lecture Notes in Computer Science* 1131, pp. 203–212, 1996.
11. F. M. Carrascal, J. M. Carreira, and M. Souto, "Automatic calculation of total lung capacity from automatically traced lung boundaries in postero-anterior and lateral digital chest radiographs," *Med. Phys.* 25, pp. 1118–1131, 1998.
12. J. Duryea and J. M. Boone, "A fully automated algorithm for the segmentation of lung fields on digital chest radiographic images," Med. Phys. 22, pp. 183–191, 1995.

What is claimed is:

1. A semi-automatic 3-D ultrasound segmentation method for displaying luminal surfaces of vessels, the method comprising the steps of:

(a) acquiring a 3-D ultrasound image of a target vessel; and (b) segmenting the luminal surfaces from said 3-D ultrasound image of said target vessel to generate a 3-D ultrasound image of the lumen of said target vessel; wherein an inflating balloon model is used for segmenting the luminal surfaces of said target vessel.

2. The method of claim 1, wherein said inflating balloon model is represented by an algorithm comprising the steps of:

(a) interactive initial placement of a balloon model with the target vessel;

(b) inflation of the model towards the target vessel wall; and (c) localization of the target vessel wall.

3. The method of claim 2, wherein said model is inflated within a user-defined volume of interest comprising a union of simple geometric shapes constructed to fit the target vessel.

4. The method of claim 3, wherein nearest neighbor interpolation is used to fill gaps between image planes.

5. The method of claim 3, wherein said balloon model is represented by a mesh of triangles placed within the target vessel.

6. The method of claim 5, wherein said model is inflated until said model represents the shape of the target vessel and then further deformed by means of image-based forces to localize the wall of the target vessel.

7. The method of claim 1, wherein said method further comprises the step of assessing the variability of the boundary of the target vessel.

8. The method of claim 7, wherein assessing the variability comprises the steps of:
   (a) generating an ensemble of meshes which span the space of selected initial balloon model placement;
   (b) determining an average segmentation boundary from the set of meshes;
   (c) determining a description of the spatial distribution of the meshes; and
   (d) computing the variance of mesh locations on the surface of the average boundary.

9. The method of claim 1, wherein said target vessel comprises any internal human or animal body channel that carries a biological fluid.

10. The method of claim 9, wherein said vessel is selected from the group consisting of blood, lymph and lacteal.

11. The method of claim 1, wherein said 3-D ultrasound image is acquired using a freehand imaging system comprising a hand-held device affixed to an ultrasound probe to track the position and orientation of the probe during scanning of the target vessel.

12. The method of claim 11, wherein digitized data from the scanning is reconstructed into a 3-D image by the steps of:
   (a) acquiring 2D images of the target vessel represented by an array of pixels;
   (b) transforming the 2D image array by a matrix to a global coordinate space into a volumetric image array comprising image slices; and
   (c) reconstructing a 3-D image one slice at a time.

13. A method for the diagnosis and prognosis of vessel disease, said method comprising the steps of:
   (a) acquiring a 3-D ultrasound image of a target vessel;
   (b) segmenting the luminal surfaces from said 3-D ultrasound image of said target vessel to generate a 3-D ultrasound image of the lumen of said target vessel using an inflating balloon model;
   (c) inspecting the generated 3-D ultrasound image of the lumen of said target vessel to assess the presence of a shadow representing a disease lesion within said lumen.

14. The method of claim 13, wherein said target vessel is a blood vessel.

* * * * *